United States Patent
Wu et al.

(10) Patent No.: US 12,411,142 B2
(45) Date of Patent: Sep. 9, 2025

(54) METHOD FOR MEASURING THE TRIMETHYLAMINE N-OXIDE PRODUCTION CAPACITY IN AN INDIVIDUAL

(71) Applicant: NATIONAL TAIWAN UNIVERSITY, Taipei (TW)

(72) Inventors: Wei-Kai Wu, Taipei (TW); Ming-Shiang Wu, Taipei (TW); Lee-Yan Sheen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 1146 days.

(21) Appl. No.: 17/268,337

(22) PCT Filed: Aug. 13, 2019

(86) PCT No.: PCT/CN2019/100312
§ 371 (c)(1),
(2) Date: Feb. 12, 2021

(87) PCT Pub. No.: WO2020/034932
PCT Pub. Date: Feb. 20, 2020

(65) Prior Publication Data
US 2021/0164999 A1 Jun. 3, 2021

Related U.S. Application Data

(60) Provisional application No. 62/717,975, filed on Aug. 13, 2018.

(51) Int. Cl.
| | | |
|---|---|---|
| *G01N 33/483* | (2006.01) | |
| *A61K 31/205* | (2006.01) | |
| *G01N 33/68* | (2006.01) | |

(52) U.S. Cl.
CPC ........ *G01N 33/6893* (2013.01); *A61K 31/205* (2013.01); *G01N 2800/042* (2013.01); *G01N 2800/044* (2013.01); *G01N 2800/323* (2013.01); *G01N 2800/50* (2013.01); *G01N 2800/52* (2013.01)

(58) Field of Classification Search
CPC ......... G01N 33/6893; G01N 2800/042; G01N 2800/044; G01N 2800/323; G01N 2800/50; G01N 2800/52; G01N 2800/32; A61K 31/205
See application file for complete search history.

(56) References Cited

U.S. PATENT DOCUMENTS 4,602,039 A * 7/1986 Cavazza .............. A61K 31/195
514/561
2017/0336379 A1 11/2017 Suslick et al.

FOREIGN PATENT DOCUMENTS

CN 104582507 A 4/2015

OTHER PUBLICATIONS

Koeth et al. (Nature Medicine,2013;vol. 19,No. 5, pp. 576-585 and online methods an supplements pp. 1-40.*
Wu et al. (Wu W-K, et al. Gut 2018;0: pp. 1-11, published Oct. 2018).*
Clinical Trial NCT01731236 (Hazen et al., 2016;retrieved from https://clinicaltrials.gov/study/NCT01731236?term=NCT01731236&rank=1&tab=history&a=3#version-content-panel).*
Demarquoy et al.Food Chemistry 86 (2004) 137-142.*
Schiattarella et al.(European Heart Journal (2017) 38, 2948-2956).*
Cho e al., Trimethylamine-N-Oxide: Friend, Foe, or Simply Caught in the Cross-Fire?, Trends in Endocrinology & Metabolism, Feb. 2017, vol. 28, No. 2, pp. 121-130. (Year: 2017).*
Koeth et al., "Intestinal Microbiota Metabolism of L-carnitine, a Nutrient in Red Meat, promotes Atherosclerosis," Nature Medicine, vol. 19, No. 5, May 31, 2013 pp. 576-582.
Lu et al., "Predicting changes of trimethylaming-N-oxide in Healthy Volunteers after choline consumption," Journal of Southern Medical University, vol. 37, No. 3, Mar. 31, 2017, pp. 290-294.

* cited by examiner

*Primary Examiner* — Gary Counts
(74) *Attorney, Agent, or Firm* — MUNCY, GEISSLER, OLDS & LOWE, P.C.

(57) ABSTRACT

The present invention provides a method for measuring the trimethylamine N-oxide (TMAO) production capacity in a subject, which comprises the following steps: (a) making the subject intake a specific dosage of carnitine; and (b) obtaining a body fluid sample of the subject at a specific time point after the subject ingests the carnitine and detecting the TMAO content in the body fluid sample. Different from the general technical detection on the market that only detects the gut microbiome composition, the invention can directly detect the ability of gut microbiota to produce TMAO in the human body. In addition, compared with directly detecting the concentration of TMAO in the blood, the invention gives a better predictive effect of gut microbiota functional phenotypes.

7 Claims, 13 Drawing Sheets

D

METHOD FOR MEASURING THE TRIMETHYLAMINE N-OXIDE PRODUCTION CAPACITY IN AN INDIVIDUAL

BACKGROUND OF THE INVENTION

1. Technical Field

The present invention relates to a method for measuring the trimethylamine N-oxide (TMAO) production capacity in an individual and more particularly to a method for measuring the TMAO production capacity in an individual by oral carnitine challenge test.

2. Description of Related Art

The gut microbiota play a critical role in the development of cardiovascular disease (CVD), and studies have shown that some micro-organism-derived metabolites produced in the intestine are involved in CVD pathogenesis. Intestinal microbial metabolites, such as trimethylamine N-oxide (TMAO), short-chain fatty acids and secondary bile acids, act as mediators in CVD-related chronic disorders such as atherosclerosis, obesity and type 2 diabetes.

L-carnitine is an abundant nutrient in meat products (especially in red meat) and functions by carrying fatty acids across the mitochondrial membrane for beta-oxidation. However, carnitine may be metabolised by gut microbiota and thereby increase the risk of cardiovascular events in patients with coronary artery disease. In the intestine, gut microbiota convert unabsorbed carnitine into trimethylamine (TMA), which is subsequently oxidised to TMAO in the liver. TMAO then enters circulation and is efficiently excreted by the kidneys. Prospective epidemiology studies have suggested a positive correlation between increased plasma TMAO levels and CVD progression. In a cohort (n=2595) of patients with coronary artery disease, high carnitine levels were associated with incident risks of myocardial infarction, stroke and death within 3 years, but only significantly in patients with concomitantly high TMAO levels. These findings may serve as a reasonable explanation for the relationship between red meat consumption and increased CVD risk. In animal studies, chronic dietary carnitine exposure increased the plasma level of TMAO, the trimethylamine (TMA) synthesis capacity of gut microbiota and the progression of atherosclerosis. The mechanism underlying the contribution of TMAO to atherosclerosis involves increased foam cell formation, decreased reverse cholesterol transport, and enhanced platelet aggregation.

Recently, the fasting plasma TMAO was also proved as a prognostic marker for both short-term and long-term incident cardiovascular events among individuals with acute coronary syndrome or stroke. Nevertheless, there remained no clear cut-off value of plasma TMAO for unfavourable outcomes. Furthermore, due to the rapid excretion of TMAO in the blood through urine and the fluctuation of blood TMAO levels, fasting blood TMAO may not be suitable as an indicator of TMAO production capacity of gut microbiome in an individual.

BRIEF SUMMARY OF THE INVENTION

The objective of the present invention is to solve the problems in the prior art as follows. Gut microbiota research technology is mainly based on the next generation sequencing to analyze the composition of bacterial species in the gut microbiota. However, the biological characteristics of most intestinal bacteria are currently unknown. Therefore, it is usually impossible to infer the functional role of gut microbiota on human health by detecting the composition of intestinal bacteria. In addition, a research team used a single measurement of the concentration of intestinal microbial metabolite TMAO in fasting blood as a method to judge the prognosis of CVD, but blood TMAO is excreted through kidney metabolism and cannot reliably represent the ability of gut microbiota to produce TMAO in the human body.

Moreover, in a dose-response meta-analysis of clinical studies, the risk of all-cause mortality increased by 7.6% per each 10 µM increment of plasma TMAO. In recent animal and human platelet aggregation studies, the concentration of plasma TMAO greater than 10-30 µM significantly enhance the thrombosis potential. However, the fasting plasma TMAO levels in subjects with normal renal function seldomly exceed 10 µM for both healthy and diseased populations.

Accordingly, a postprandial plasma TMAO might theoretically reflect the pathophysiological level of TMAO. Thus, this invention establishes an oral carnitine challenge test (OCCT) to simulate the postprandial plasma TMAO as well as functionally measure the TMAO synthesis capacity from host-diet-microbiota interactions.

The present invention provides a method for measuring the trimethylamine N-oxide (TMAO) production capacity in a subject, which comprises the following steps: (a) making the subject ingestion of a specific dosage of carnitine; and (b) obtaining a body fluid sample of the subject at a specific time point after the subject ingests the carnitine and detecting the TMAO content in the body fluid sample.

In a preferred embodiment, the specific dosage is 1000-2000 mg.

In a preferred embodiment, the carnitine is L-carnitine.

In a preferred embodiment, the L-carnitine is in the form of L-carnitine fumarate.

In a preferred embodiment, the subject fasts for at least 8 hours before step (a), a fasting body fluid sample of the subject is obtained before step (a), and the TMAO content of the fasting body fluid sample is measured and used as a reference point of the TMAO content of the subject before OCCT.

In a preferred embodiment, the specific time point is 4 hours, 8 hours, 12 hours, 24 hours, 36 hours and 48 hours after the subject ingests the carnitine.

In a preferred embodiment, the specific time point is 24 hours and 48 hours after the subject ingests the carnitine.

In a preferred embodiment, the subject is prohibited from eating foods rich in carnitine at a specific time point after ingesting the carnitine.

In a preferred embodiment, the body fluid sample of the subject is blood or urine.

In a preferred embodiment, the TMAO content is related to cardiovascular disease, therapeutic drug effect assessment, and personalized diet.

The method of the present invention for measuring the trimethylamine N-oxide production capacity in an individual has the following advantages:

1. The method of the present invention can calculate the ability of the gut microbiome to produce TMAO in a subject by oral carnitine challenge test, i.e. by making the subject intake a specific dosage of carnitine and then detecting the TMAO level of the body fluid sample such as blood and/or urine at a specific time point.

2. In the method of the present invention, at the same sample collection time point, the TMAO level of blood is highly correlated with the TMAO level of urine. That is, urine samples can be used instead of blood samples for the clinical application of oral carnitine challenge test.

3. In the method of the present invention, the detection result of the oral carnitine challenge test can be used as a reference basis for the development of novel microbial markers related to TMAO production.

4. The method of the present invention does not need to use isotope-labelled carnitine.

According to the above, the method of the present invention can be used as a clinically functional detection method of human gut microbiota, which can be used to identify the ability of a subject's gut microbiome to metabolize carnitine and generate trimethylamine N-oxide in the human body, and therefore to assess the risk of cardiovascular disease caused by the gut microbiome of the subject. The detection results can provide clinical applications such as dietary advice and drug treatment reference for the subjects, and can provide the research direction of biomarkers related to gut microbiota and trimethylamine N-oxide production.

DETAILED DESCRIPTION OF THE INVENTION

The details and technical solution of the present invention are hereunder described with reference to accompanying drawings. For illustrative sake, the accompanying drawings are not drawn to scale. The accompanying drawings and the scale thereof are not restrictive of the invention.

The use of "or" means "and/or" unless stated otherwise. The use of "comprise" means not excluding the presence or addition of one or more other components, steps, operations, and/or elements to the described components, steps, operations, and/or elements. The terms "Comprising," "having," "containing" and "including" are interchangeable without limitation.

The terms "a" and "an" refer to one or to more than one (i.e., to at least one) of the grammatical object of the specification. Similarly, as used herein and in the appended claims, the singular forms "a," "an," and "the" include plural referents unless the context dictates otherwise.

Unless defined otherwise, all technical and scientific terms used herein have the same meaning as commonly understood to one of ordinary skill in the art to which this disclosure belongs. In addition, the following terms used in this application have the following meanings.

Figure 1:
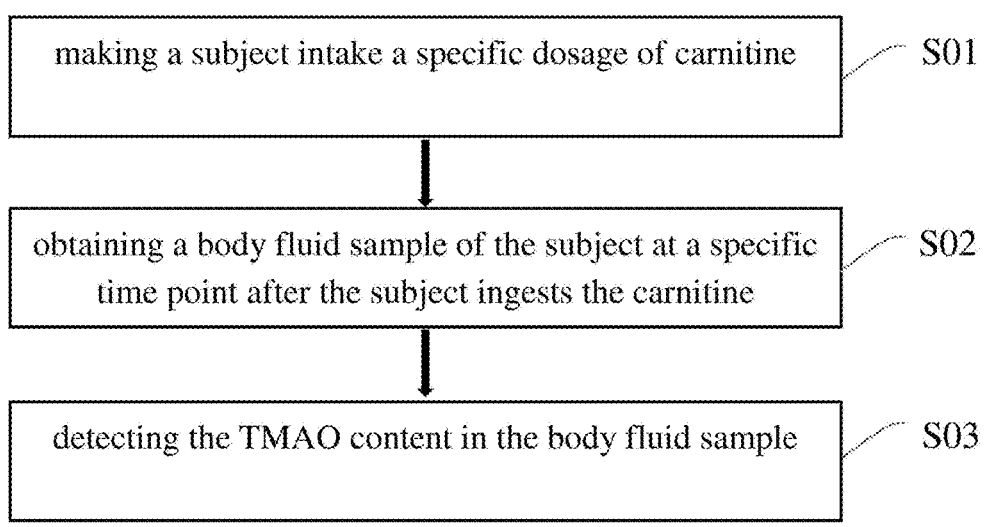
FIG. 1 shows a schematic flowchart according to a preferred embodiment of the present invention.
Figure 2:
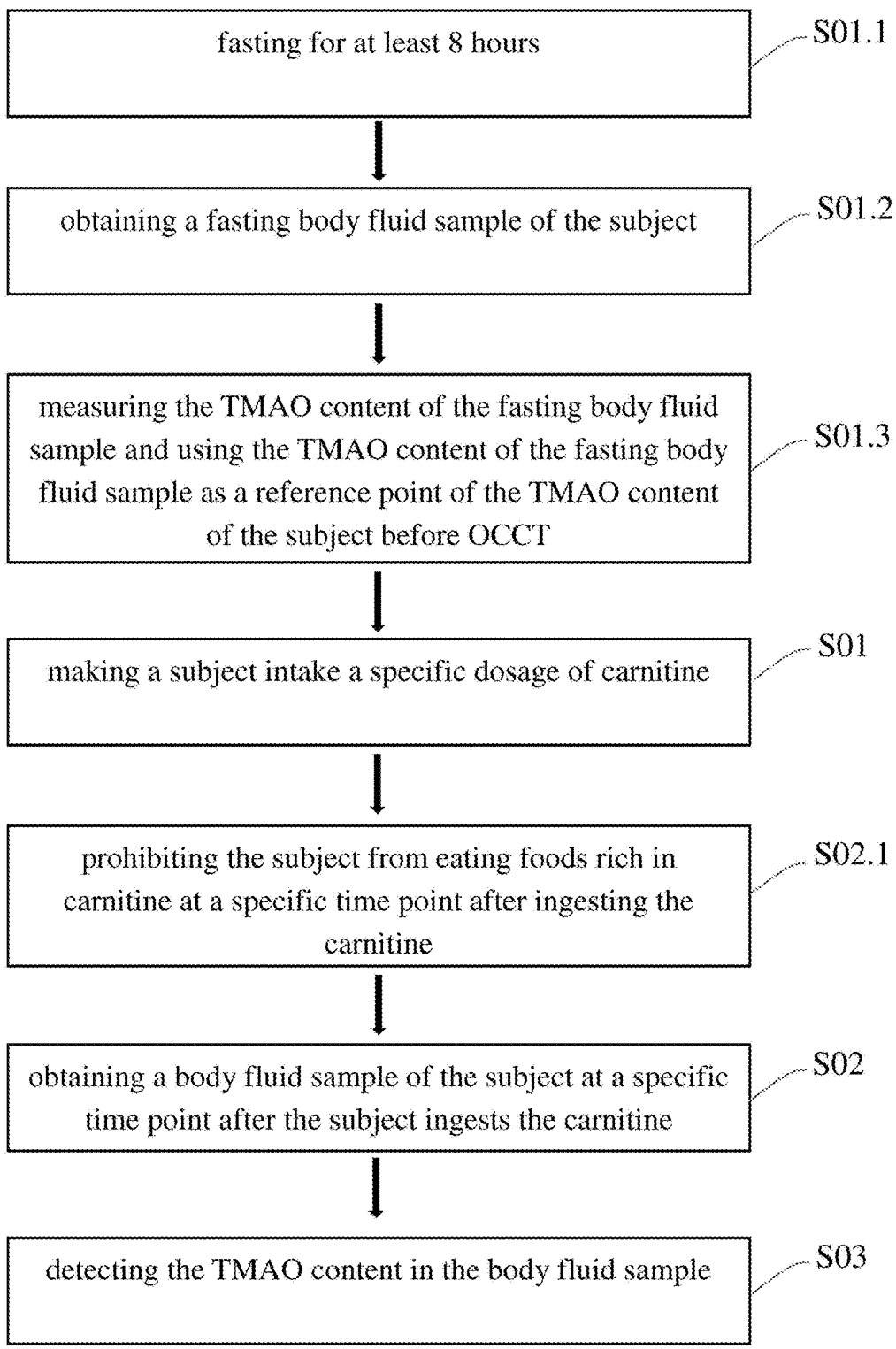
FIG. 2 shows a schematic flowchart according to another preferred embodiment of the present invention.

Please refer to FIG. 1 and FIG. 2 for schematic flowcharts according to preferred embodiments of the present invention.

As shown in FIG. 1, the present invention provides a method for measuring the trimethylamine N-oxide (TMAO) production capacity in a subject, which comprises the following steps: (a) making the subject intake a specific dosage of carnitine (S01); and (b) obtaining a body fluid sample of the subject at a specific time point after the subject ingests the carnitine (S02) and detecting the TMAO content in the body fluid sample (S03).

As shown in FIG. 2, in a preferred embodiment, the subject fasts for at least 8 hours before step (a) (S01.1), a fasting body fluid sample of the subject is obtained before step (a) (S01.2), and the TMAO content of the fasting body fluid sample is measured and used as a reference point of the TMAO content of the subject before OCCT (S01.3); then proceed to step (a) to make the subject intake a specific dosage of carnitine (S01). In a preferred embodiment, before step (b), the subject is prohibited from eating foods rich in carnitine at a specific time point after ingesting the carnitine (S02.1); then step (b) is performed on the subject: obtaining a body fluid sample of the subject at a specific time point after the subject ingests the carnitine (S02) and detecting the TMAO content in the body fluid sample (S03).

The carnitine described herein is an amino acid derivative whose function is to carry fatty acids across the inner mitochondrial membrane for (3-oxidation. Carnitine includes two stereoisomers, namely L-carnitine and D-carnitine. In a preferred embodiment, the carnitine in the oral carnitine challenge test (OCCT) used in the method of the present invention is L-carnitine. In a preferred embodiment, the carnitine in the OCCT used in the method of the present invention is in the form of L-carnitine fumarate.

Carnitine is a nutrient rich in meat products, so the carnitine-rich foods described herein refer to meat foods and/or meat products, especially red meat and seafood, and may further include dairy products. The aforementioned red meat refers to meat that is red before cooking, such as but not limited to mammalian meat such as pork, beef, mutton, and venison. The aforementioned seafood includes, but is not limited to, fish, crustaceans (such as shrimp and crab), shellfish, mollusks, echinoderms, and kelp. The seafood mentioned herein is not limited to fresh seafood, but also includes dried and dehydrated seafood.

The way of ingesting carnitine for oral carnitine challenge test described in step (a) herein is preferably to obtain a specific amount of carnitine in the form of oral administration. However, this specification does not exclude other methods such as injections instead of oral administration to perform a carnitine challenge test equivalent to oral carnitine challenge test. In a preferred embodiment, in step (a) of the present invention, the specific dosage of carnitine taken by the subject is 1000 to 2000 mg, such as but not limited to 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg or 2000 mg.

Carnitine may be metabolized by gut microbiota. In the intestine, gut microbiota convert unabsorbed carnitine into trimethylamine (TMA), which is subsequently oxidised to TMAO by flavin monooxygenase (FMO3) in the liver. The trimethylamine N-oxide (TMAO) mentioned herein refers to the product produced after carnitine is transformed by the gut microbiome in an individual and metabolized by the liver. Carnitine metabolising bacteria are, for example, but not limited to, bacteria containing cntA/B, such as *E. coli, Klebsiella* spp, *Citrobacter* spp and so on. The present invention finds that urinary excretion and eating habits affect TMAO fluctuations in individuals. The intra-individual TMAO values acquired from OCCT helps to reveal the pathophysiological levels of plasma TMAO from daily diet-microbiota interactions. In a preferred embodiment, the TMAO content determined by the method of the present invention is related to cardiovascular disease, therapeutic drug effect assessment, and personalized diet.

In step (b) of the present invention, a body fluid sample of the subject is obtained at a specific time point after the subject ingests the carnitine. The "specific time point" mentioned herein is at least one time point selected from the group consisting of 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours and 72 hours after the subject ingests the carnitine. In a preferred embodiment, the specific time point is 24 hours and 48 hours after the subject ingests the carnitine.

The body fluid sample described herein includes, but is not limited to, blood, cerebrospinal fluid, peritoneal fluid, pleural fluid, synovial fluid, dialysate, amniotic fluid, bronchial aspirate, bronchoalveolar lavage fluid, bile, umbilical blood, duodenal fluid, fungal blood culture, urine collected with indwelling urinary catheter, gastric juice, lymphatic fluid, nasopharyngeal aspirate, urine collected with percutaneous nephrostomy, semen, sputum, sweat, urine, vaginal secretion or blister fluid. In a preferred embodiment, the body fluid sample of the subject is blood or urine.

Hereinafter, the present invention will be further described with detailed description and embodiments. However, it should be understood that these embodiments are only used to facilitate easier understanding of the invention and not to limit the scope of the invention.

Example 1—Plasma Samples

In this example, pharmacokinetics was used to optimize the OCCT conditions, and individuals with different dietary habits (omnivores and vegetarians) (hereinafter also referred to as subjects) are recruited for confirmation experiments. In this example, the faecal samples of 57 subjects were respectively subjected to 16S rDNA sequencing analysis to obtain the gut microbiome compositions, which were integrated with OCCT result values, host genotypes, dietary records and serum biochemistry.

A. Materials and Methods

Omnivore and vegetarian study populations: 57 healthy volunteers (23 vegetarians and vegans and 34 omnivores) were recruited. In this example, participants who self-reported not having eaten any meat or seafood products for prior 2 years or longer were defined as vegetarians. All participants were screened using a health history questionnaire. Inclusion criteria were as follows: (1) age≥20 years and (2) no exposure to antibiotics, probiotics or carnitine supplements within the previous month. Participants were excluded from the study if they reported recent gastrointestinal discomfort (such as abdominal pain or diarrhoea) or a history of chronic diseases including myasthenia gravis, diabetes mellitus, chronic renal disease, hyperparathyroidism, epilepsy and severe anaemia. Each participant completed a FFQ for dietary assessment and signed a waiver of informed consent provided by the Institutional Review Board of National Taiwan University Hospital.

Dietary assessments: The participants' diets were assessed using a semiquantitative FFQ. The FFQ used in this example was validated in a previous study; the questionnaire exhibited reliability and validity for identifying major nutrients in the diets of Taiwanese vegetarians and omnivores. In this example, the nutrient analysis programme used to calculate the results of the FFQ was based on Taiwan's Food Composition Database. Carnitine intake was calculated on the basis of values published previously. The intake of nutrients and food groups were standardised to z-scores by using linear regression adjusted for total calorie intake with residual values centred.

Oral carnitine challenge test (OCCT): All the participants fasted overnight (>8 hours) before the OCCT. Fasting blood and spot urine samples were collected as baseline, and three tablets of L-carnitine fumarate (GNC) were then administered orally to the participants. Subsequently, the participants underwent time-series blood drawings with concurrent spot urine collections at 24 hours and 48 hours after the oral carnitine challenge. The participants were requested to provide urine samples within 2 hours of blood sample collections. All the participants were asked to avoid red meat, seafood and any medication during the period of the carnitine challenge test. The plasma and urine samples were aliquoted after centrifugation at 3000 rpm and stored in a freezer at −20° C. Ten carnitine tablets (GNC) were examined through HPLC to verify the amount of L-carnitine used in the OCCT. The mean dose of carnitine fumarate in each tablet was 693.5 (SD±63.2) mg (≈400 mg L-carnitine/tablet).

Pharmacokinetic study of plasma TMAO by oral administration of carnitine: Thirteen independent volunteers were recruited for a pharmacokinetic study of the OCCT. After the oral carnitine challenge, blood samples were collected at 4, 8, 12, 24, 36 and 48 hours. Six of the volunteers agreed to participate in the same pharmacokinetic test again 3 months later. All the volunteers signed informed consent waivers provided by the Institutional Review Board of National Taiwan University Hospital.

Statistical analysis: Two-tailed Student's t-test or a Wilcoxon non-parametric test were used to compare group means as considered appropriate. The odds ratio (OR) of omnivores versus vegetarians as being high TMAO producers and corresponding 95% confidence intervals (CI) were calculated using logistic regression model. The Pearson's correlation was used to calculate association between two variables. All statistics were analysed using R software V.3.4.1 or GraphPad Prism (V.7).

B. Result 1:

The content of carnitine in the individuals' plasma: A comparison of demographic data and biochemical values revealed significant differences in several metabolic parameters, namely, plasma carnitine, serum total cholesterol, low-density lipoprotein, urea nitrogen, fasting glucose and aspartate transaminase levels, between the omnivores and vegetarians (table 1). Of the compared parameters, carnitine and cholesterol levels between the omnivores and vegetarians exhibited the most significant differences (p<0.0001). However, the urine carnitine level between the omnivores and vegetarians did not exhibit a significant difference. In general, the urine TMAO level was remarkably higher than the plasma TMAO level, whereas carnitine was more abundant in plasma samples. This finding may indicate that the human body tends to preserve carnitine as a nutrient and excrete TMAO as waste through the urinary system. Fasting TMAO levels in blood and urine were both higher in the omnivores (blood: 3.54±0.96 µM; urine: 68.13±20.70 nmol/mmol) than in the vegetarians (blood: 1.87±0.21 µM; urine: 33.98±3.49 nmol/mmol); however, the differences did not reach statistical significance (table 1).

TABLE 1

|  | Vegetarian (n = 23) | Omnivore (n = 34) | P values |
|---|---|---|---|
| Female (n (%)) | 14 (65) | 24 (71) |  |
| Age (years) | 34.13 ± 1.70 | 30.18 ± 1.30 | 0.0665 |
| BMI (kg/m$^2$) | 22.40 ± 0.55 | 21.81 ± 0.57 | 0.4793 |
| Genotype FMO3-SNP (n (%)) | | | |
| Glu158Lys - AAG | 6 (26.1) | 8 (23.5) |  |
| Glu308Gly - GGG | 6 (26.1) | 8 (23.5) |  |
| Plasma | | | |

TABLE 1-continued

|  | Vegetarian (n = 23) | Omnivore (n = 34) | P values |
|---|---|---|---|
| Glucose-AC (mg/dL) | 69.39 ± 2.20 | 75.41 ± 1.91 | 0.0459 |
| AST (U/L) | 11.30 ± 1.036 | 15.29 ± 1.19 | 0.0211 |
| ALT (U/L) | 7.22 ± 0.94 | 12.91 ± 2.38 | 0.0627 |
| BUN (mg/dL) | 9.57 ± 0.65 | 11.63 ± 0.50 | 0.0145 |
| Creatinine (mg/dL) | 0.55 ± 0.03 | 0.60 ± 0.02 | 0.2041 |
| T-cholesterol (mg/dL) | 140.50 ± 4.27 | 174.90 ± 5.23 | <0.0001 |
| Triglyceride (mg/dL) | 89.13 ± 11.31 | 88.32 ± 10.07 | 0.9584 |
| LDL-C (mg/dL) | 75.13 ± 4.25 | 97.44 ± 4.64 | 0.0014 |
| hsCRP (mg/dL) | 0.06 ± 0.01 | 0.18 ± 0.09 | 0.2766 |
| TMAO (μM) | 1.87 ± 0.21 | 3.54 ± 0.96 | 0.1618 |
| Carnitine (μM) | 34.72 ± 3.07 | 63.46 ± 5.08 | <0.0001 |
| Urine |  |  |  |
| TMAO (nmol/mmol Cr) | 33.98 ± 3.49 | 68.13 ± 20.70 | 0.1843 |
| Carnitine (nmol/mmol Cr) | 2.52 ± 0.64 | 15.37 ± 6.35 | 0.1035 |

*The p value is from the comparison between vegetarian and omnivore volunteers using Student's t-test. Values are the mean ± SEM.
AST, aspartate aminotransferase; ALT, alanine aminotransferase; BMI, body mass index; BUN, blood urea nitrogen; Cr, creatinine; FMO3, flavin monooxygenase; hsCRP, high-sensitivity C reactive protein; LDL-C, low-density lipoprotein cholesterol; TMAO, trimethylamine N-oxide.

Figure 3:
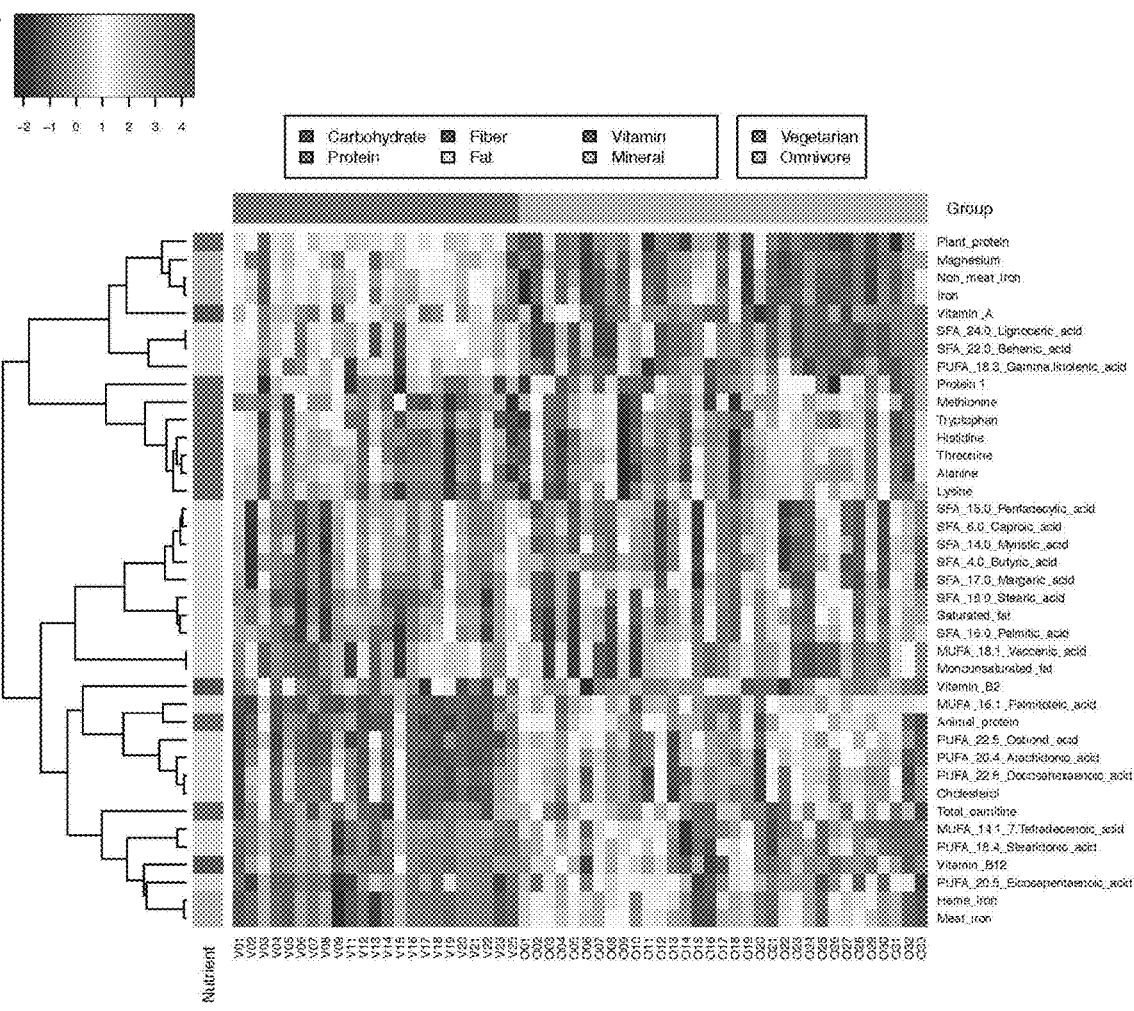
FIG. 3 shows a preferred embodiment of the present invention, which shows that the divergence of dietary patterns between vegetarian and omnivore contributed no significant differences for gut microbiome composition and diversity. (A) Heatmap of dietary micronutrients in omnivores versus vegetarians (q value<0.1) with clustering nutrients color labelled by six nutrient categories. Red=higher abundance, blue=lower abundance. (B) The carnitine and cholesterol consumption levels of vegetarians and omnivores exhibited highly significant differences. (C) The principle component analysis of food frequency questionnaire (FFQ) nutrients data indicated significantly divergent patterns between omnivores and vegetarians (permutational multivariate analysis of variance (PERMANOVA): p<0.001). (D) Compositional profiling of gut microbiota in vegetarians and omnivores revealed no significant difference (PERMANOVA: p=0.3528) demonstrated by principle coordinate analysis calculated using Bray-Curtis distance. (E) Comparison of alpha diversity index in vegetarians versus omnivores. (F) The Firmicutes/Bacteroidetes (F/B) ratio in omnivores versus vegetarians exhibited no significant difference. Data in all bar plots are expressed as mean±SEM. All statistics in bar plots and box plots were analysed by Student's t-test.
Figure 3:
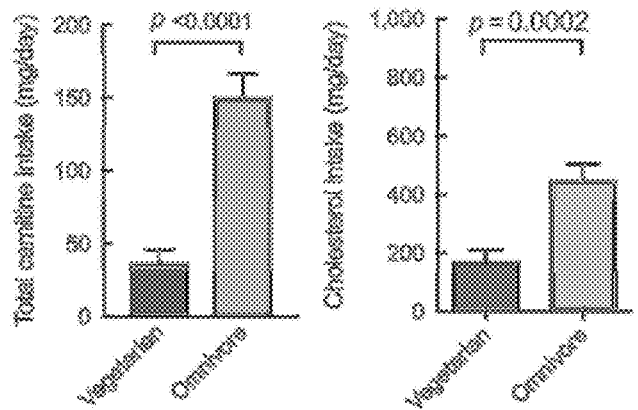
Figure 3:
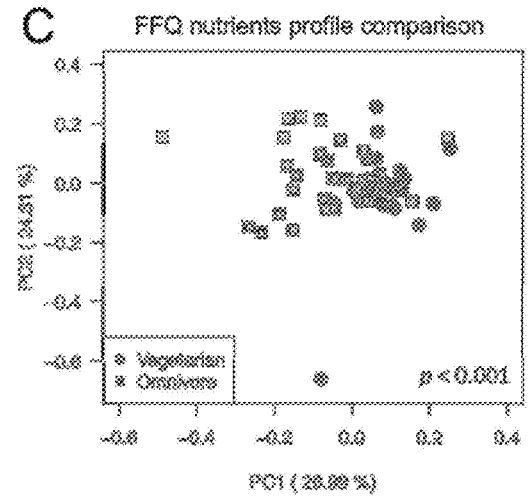
Figure 3:
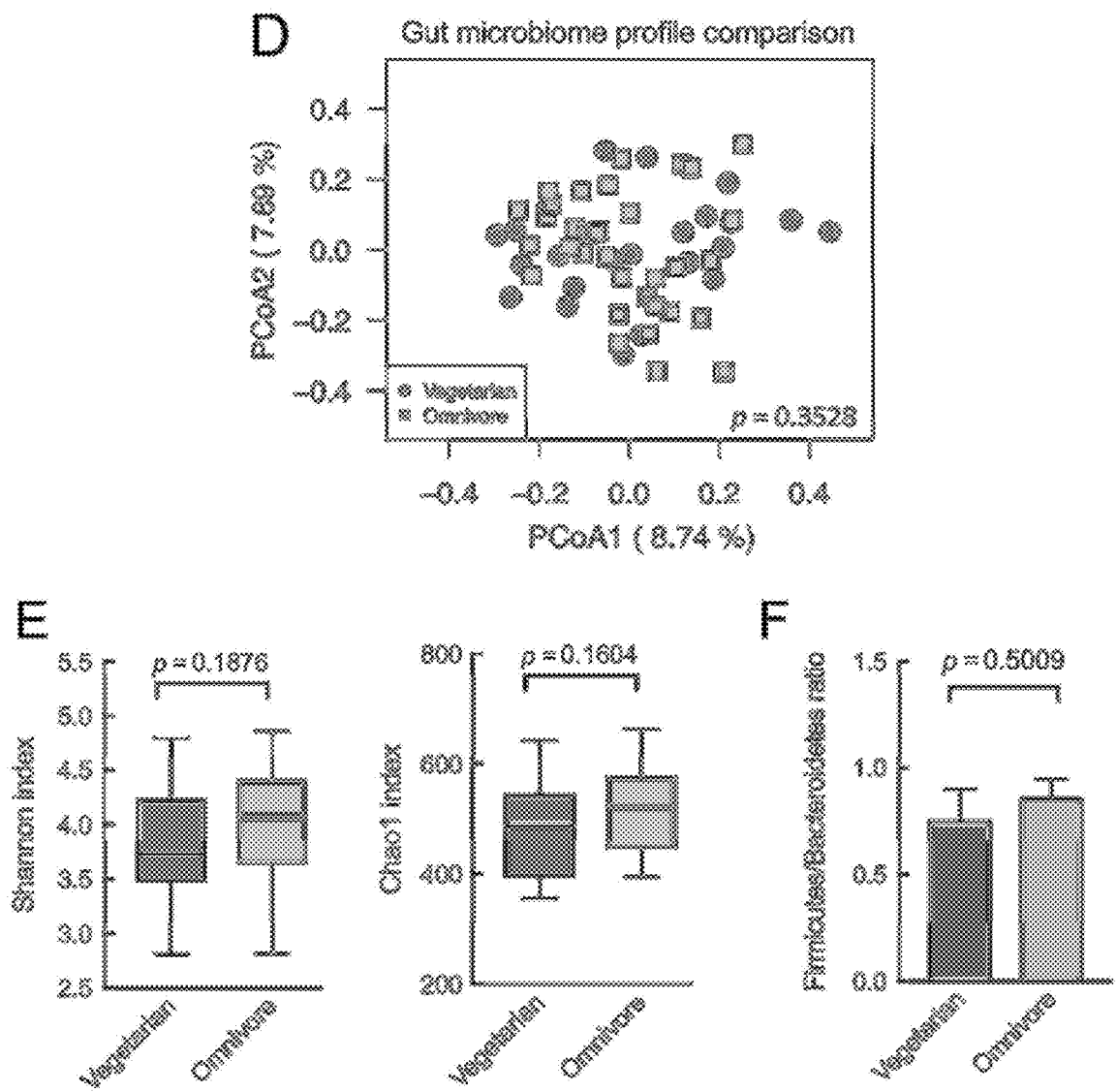

Markedly different dietary patterns between omnivores and vegetarians contributed to minor difference in gut microbiome: Among 87 nutrient levels calculated using the food frequency questionnaire (FFQ), 43 differed significantly between the omnivores and vegetarians (p<0.05) with false discovery rate (FDR)<0.1. The omnivores consumed more cholesterol, carnitine, saturated fat and animal protein than did the vegetarians (FIGS. 3A and 3B). Thus, the omnivores exhibited higher serum cholesterol, carnitine, LDL and urea nitrogen levels (table 1). The results of the principle component analysis of all the nutrients calculated using the FFQ also showed distinct dietary patterns between the omnivores and vegetarians (FIG. 3C). However, gut microbiome profiles and indicators between the omnivores and vegetarians did not considerably differ according to the results of the principle coordinate analysis, alpha diversity and Firmicutes/Bacteroidetes (F/B) ratio (FIG. 3D-3F), although moderately significant differences in minor gut microbiome communities (<2% species) were identified. The results of the linear discriminant analysis effect size (LEfSe) analysis revealed that Prevotellaceae was prevalent in the vegetarians' gut microbiome, whereas the gut microbiome of the omnivores featured characteristic taxa of Clostridiaceae, Bacteroidales S24 and Eubacterium. These findings are consistent with those of previous studies.

Figure 4:
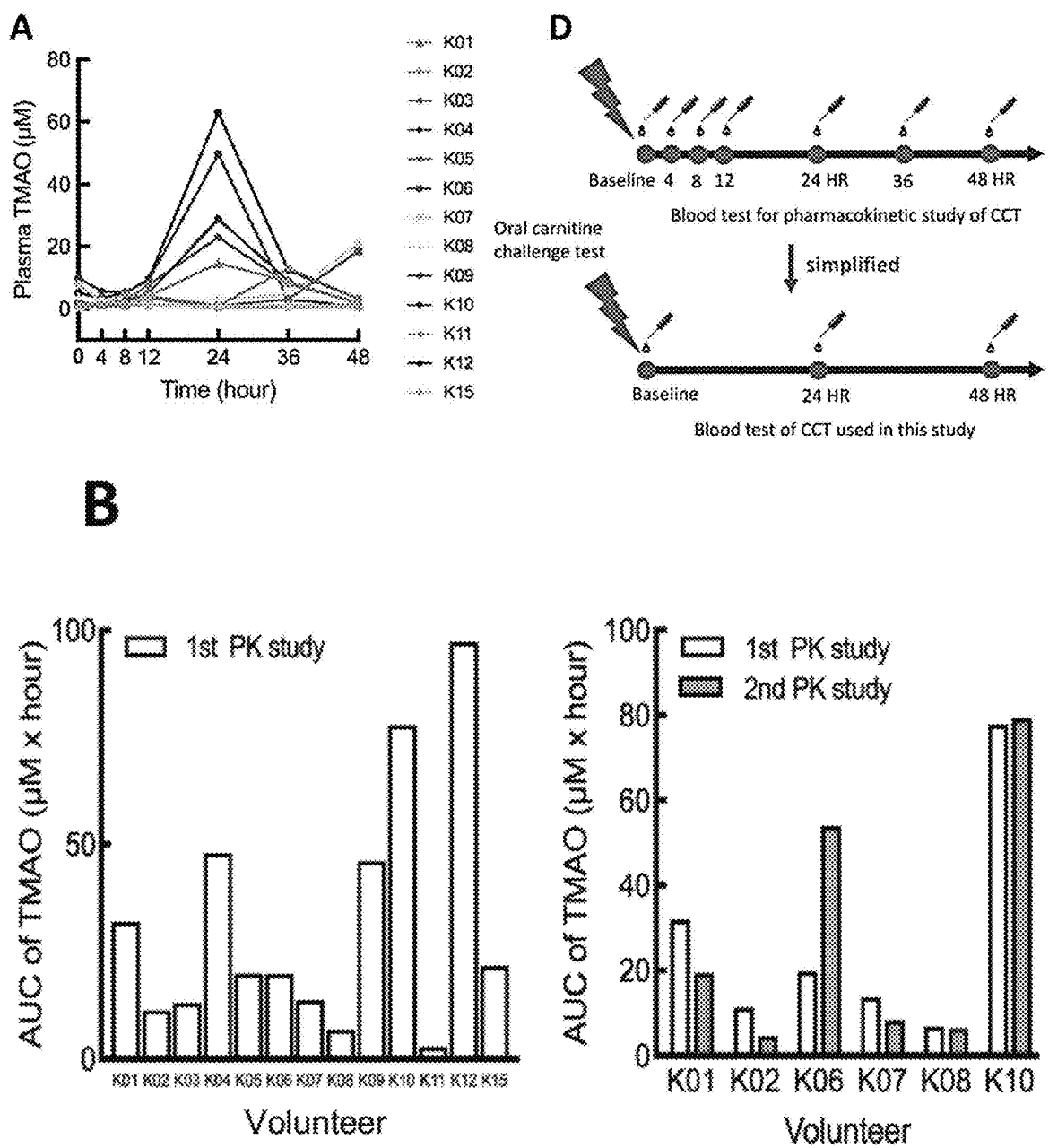
FIG. 4 shows a preferred embodiment of the present invention, which shows the pharmacokinetic (PK) study of OCCT. (A) Thirteen volunteers were recruited for a PK study of the OCCT. Each participant received three tablets of GNC L-carnitine (approximately 1200 mg L-carnitine) and blood drawings at $4^{th}$ hour, $8^{th}$ hour, $12^{th}$ hour, $24^{th}$ hour, $36^{th}$ hour and $48^{th}$ hour. (B) The bar plots of AUC in OCCT for different volunteers and the same volunteer with different PK studies (six volunteers received the second PK study 3 months later). (C) Normalised dissimilarity of AUC of different PK studies in the same and different individuals (defined as |AUC1−AUC2|/[AUC1+AUC2]). AUC1: AUCs of $1^{st}$ PK study; AUC2: AUCs of second PK study. These data suggested the trend of TMAO production capacity is reproducible in the same individual periodically. (D) Validation and simplification of sample collection time points for the OCCT according to the results of PK studies. AUC, area under the curve; CCT, carnitine challenge test; TMAO, trimethylamine N-oxide.
Figure 4:
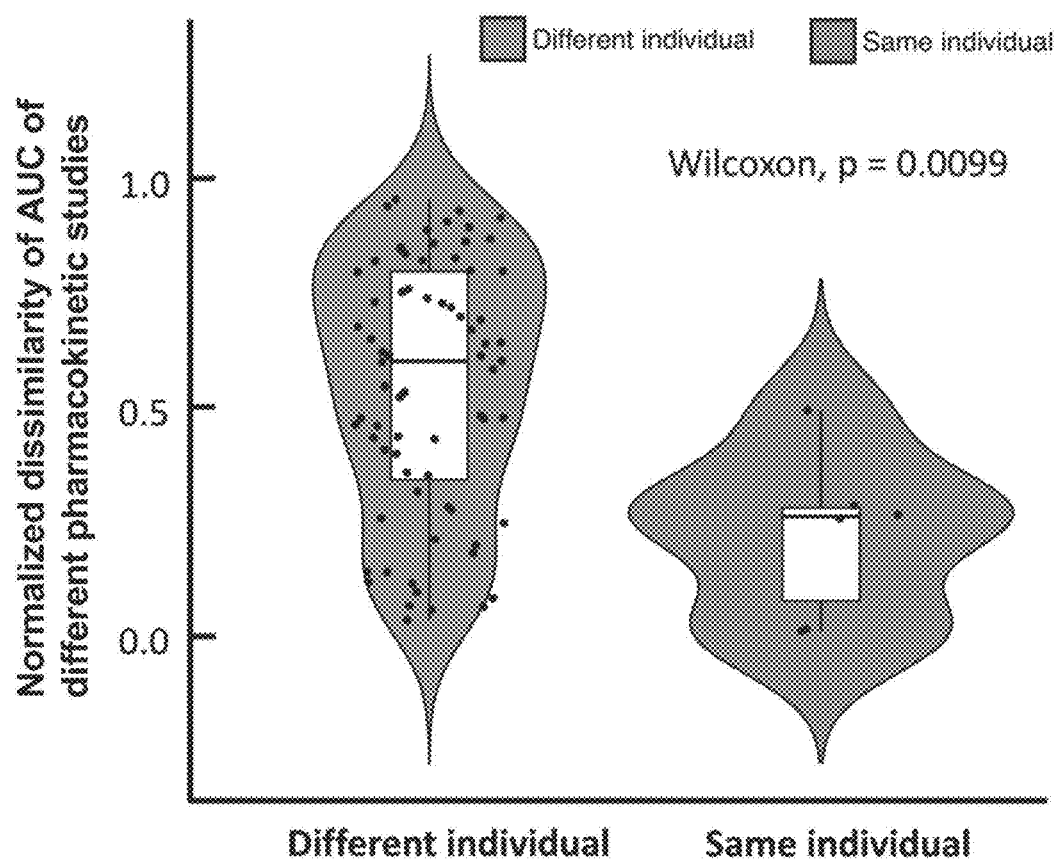

Plasma TMAO peaked in the interval between 24 hours and 48 hours of the OCCT: This example assumed that TMAO formation in blood occurred at approximately 24 hours of the OCCT based on the time required for bowel transit, microbial catabolism and the enzymatic reaction of hepatic FMO3 to convert the ingested carnitine into plasma TMAO. The example performed a pharmacokinetic study of the OCCT to confirm this hypothesis (FIG. 4). In the study, 13 participants received seven blood tests at indicated time points after ingestion of three tablets of L-carnitine fumarate (General Nutrition Centers (GNC), Pennsylvania, USA). The carnitine amount of each tablet was verified through high-performance liquid chromatography (HPLC) to ensure that the dose of L-carnitine in each test was consistent. After the OCCT, plasma TMAO levels remained stable at trough levels for 12 hours and peaks started to present after 24 hours (FIG. 4A). The plasma carnitine level peaked at 4 hours after OCCT while TMA and γ-butyrobetaine in the plasma remained at very low concentration. Among the 13 participants, 6 participated in an additional pharmacokinetic study 3 months later, and the original trends and values for each individual were reproduced in the results (FIGS. 4B and 4C). Thus, the OCCT was simplified to involve three sample collection times: the baseline (fasting plasma TMAO), 24 hours and 48 hours (FIG. 4D).

Figure 5:
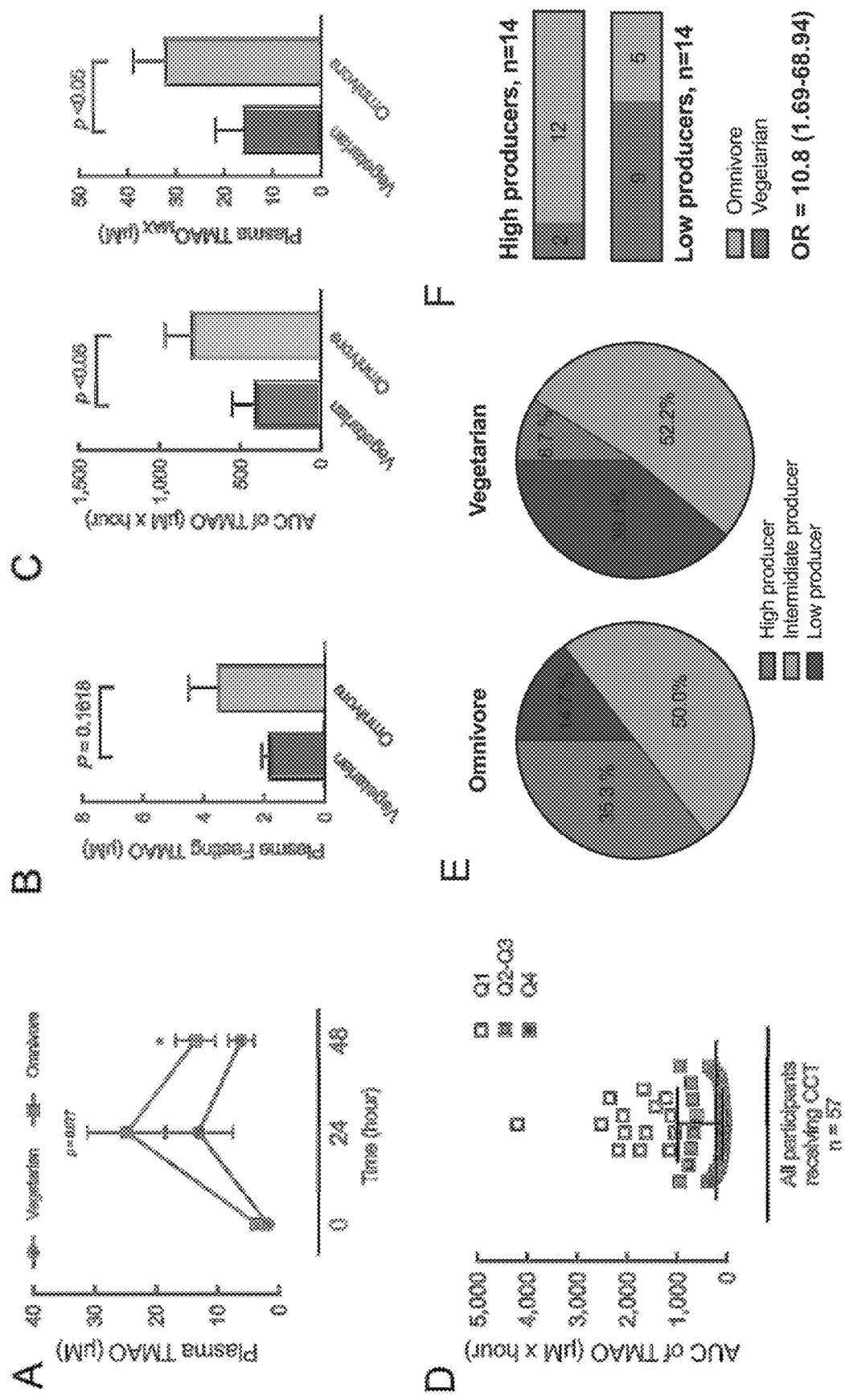
FIG. 5 shows a preferred embodiment of the present invention, which shows that omnivores and vegetarians exhibited different levels of ability to transform L-carnitine into TMAO in the body. (A) The method of the present invention was administered to 23 vegetarians and 34 omnivores. The differences in plasma TMAO levels between the vegetarians and omnivores appeared at 24 hours and 48 hours compared with baseline. Data are expressed as mean±SEM; *p<0.05. (B) No significant difference of fasting plasma TMAO levels was noted between the vegetarian and omnivore groups. (C) The AUC values and maximum values of the OCCT for the omnivores were both significantly higher than for the vegetarians. (D) The population was grouped into four quartiles according to the AUC values of the OCCT. The Q4 population was defined as high TMAO producers, the Q1 as low producers and Q2-Q3 as intermediate producers. (E) 35.3% of the omnivores were grouped as high TMAO producers compared with 8.7% of the vegetarians. 14.7% of the omnivores were grouped as low producers compared with 39.1% of the vegetarians. (F) Among the high producers, 12/14 (86%) were omnivores, whereas among the low producers, 5/14 (36%) were omnivores. The ORs of omnivores versus vegetarians as being high TMAO producers is 10.8 (95% CI 1.69 to 68.94). Plasma TMAO levels at indicated times in OCCT and plasma fasting TMAO data were analysed by Student's t-test. AUC of TMAO and TMAOMAX in OCCT were analysed by Mann-Whitney U test.

OCCT effectively differentiated gut microbiota-mediated TMAO production capacity between the omnivore and vegetarian groups: Through the method of the present invention, differences in fasting plasma TMAO levels between the omnivores and vegetarians were moderate. Therefore, the OCCT provided in this example can be used to determine individual TMAO production capacity as mediated by gut microbiota. All the omnivore and vegetarian volunteers participated in a simplified OCCT with blood and urine collection at baseline, 24 hours and 48 hours. In the OCCT curve, plasma TMAO levels in the omnivores versus vegetarians diverged at 24 hours and 48 hours, but fasting TMAO levels remained similar (FIGS. 5A and 5B). In contrast to the values of fasting TMAO, those of the area under the curve (AUC) and the maximum values of the OCCT were significantly higher in the omnivores than in the vegetarians (FIG. 5C).

Omnivores were more likely to be high TMAO producers than the vegetarians: To define the functional phenotype of gut microbiota for TMAO production, the example plotted the AUC values from the OCCT results for all the 57 participants and grouped the values into quartiles. The 14 participants with Q1-level AUC values were labelled as low TMAO producers, and the 14 participants in Q4 were labelled as high TMAO producers (FIG. 5D). The participants with levels in between Q1 and Q4 were labelled as intermediate producers. Among the omnivore participants, 35.3% were grouped as high TMAO producers and 14.7% were grouped as low TMAO producers. By contrast, only 8.7% of the vegetarians were grouped as high TMAO producers and 39.1% were grouped as low TMAO producers (FIG. 5E). With regard to TMAO production phenotypes defined by the OCCT, the participants in the omnivore group exhibited a 10-fold OR (OR: 10.8, 95% CI 1.69 to 68.94) of being a high TMAO producer compared with the vegetarian group (FIG. 5F). However, despite long-term adherence to a strict vegetarian diet (>10 years), some vegetarians exhibited considerable TMAO production when high doses of carnitine were consumed.

Figure 6:
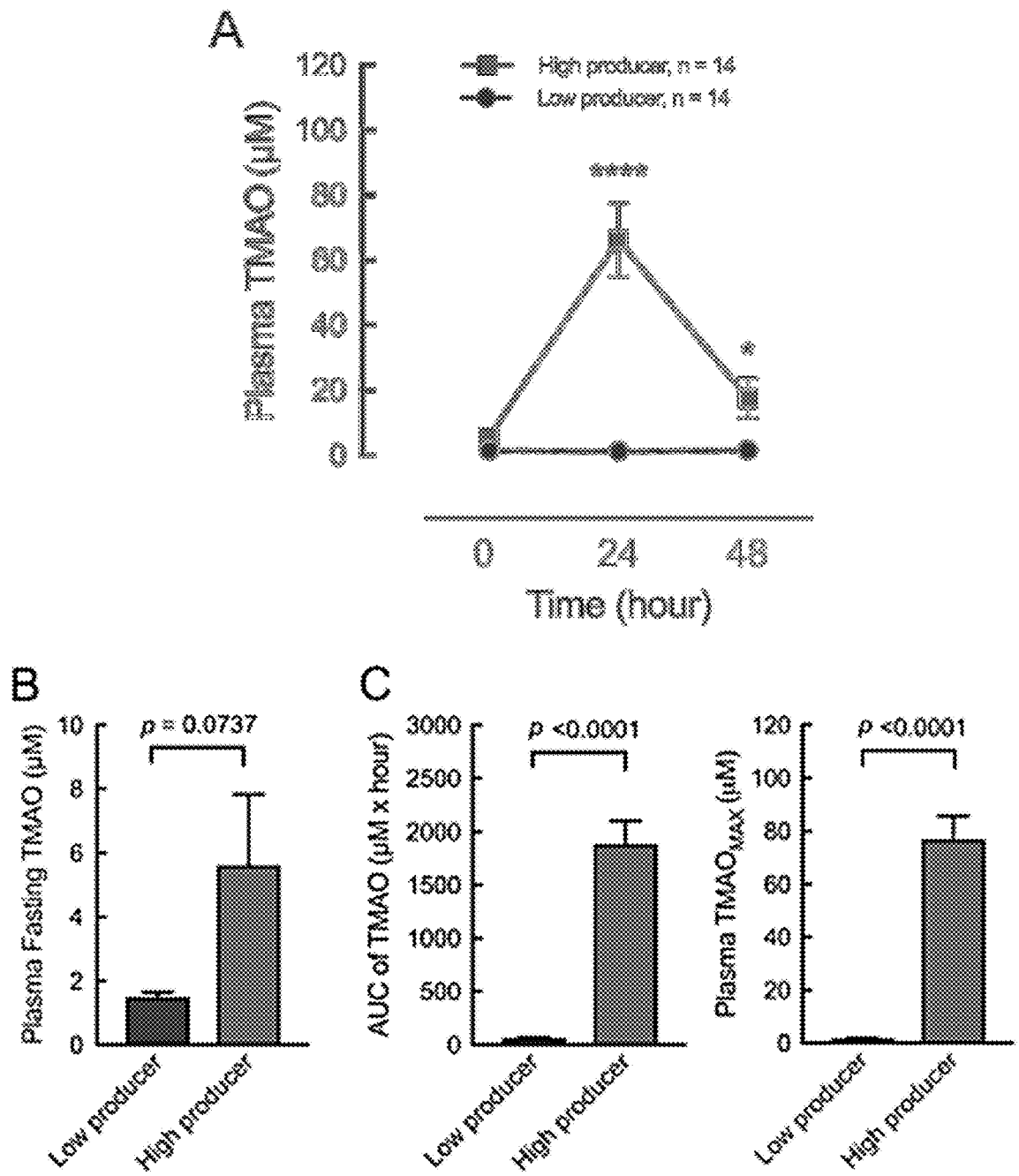
FIG. 6 shows a preferred embodiment of the present invention, which shows that the functional phenotypes grouped by OCCT were significantly associated with the differences of gut microbiome composition, diversity, features and functions. (A) The high TMAO producers and low producers corresponded with distinct curves for the OCCT. Data are expressed as mean±SEM. (B) The difference in plasma fasting TMAO levels between the high producers and low producers was moderately significant. (C) The differences in AUC values and maximum OCCT values were highly distinct. (D) Heatmap demonstration of hierarchical clustering levels of bacterial taxa significantly differentiated (p<0.01) between the high and low TMAO producers. The heatmap displayed relatively higher taxa in Firmicutes phylum (pink) in high TMAO producers compared with low producers, and opposite results were indicated for the Bacteroidetes phylum (yellowish). (E) The Firmicutes/Bacteroidetes (F/B) ratio between low producers versus high producers was significantly different. (F) The alpha diversity of Shannon index and Chao1 index between the high TMAO producers and low producers was also significantly different. (G) Principle coordinate analysis of the gut microbiome profiles of the TMAO high producers versus low producers indicated a significant difference. (H) The characteristic phylogenetic taxa in the TMAO high producers versus low producers ranked by the linear discriminant analysis (LDA) score exhibited similarities to taxa (marked in the red frame) detected in previous well-controlled mouse studies. (I) Eight 9-week-old male germ-free mice (n=4 in each group) received faecal microbiota transplantation from a high-TMAO-producer or low-TMAO-producer donor as a humanised gnotobiotic mice model. The mice were placed with carnitine supplement diet (1.3% in water) and received a d9-carnitine challenge test through oral gavage. The phenotypes of TMAO-producing ability of donors were significantly reproduced in the mice. Data are expressed as mean±SEM. Plasma TMAO levels at indicated times in OCCT, plasma fasting TMAO, F/B ratio, Shannon and Chao1 index, plasma d9-TMAO and d9-TMA data were analysed by Student's t-test. AUC of TMAO and TMAOMAX in OCCT were analysed by Mann-Whitney U test; *p<0.05, p<0.01, *p<0.001, ****p<0.0001.
Figure 6:
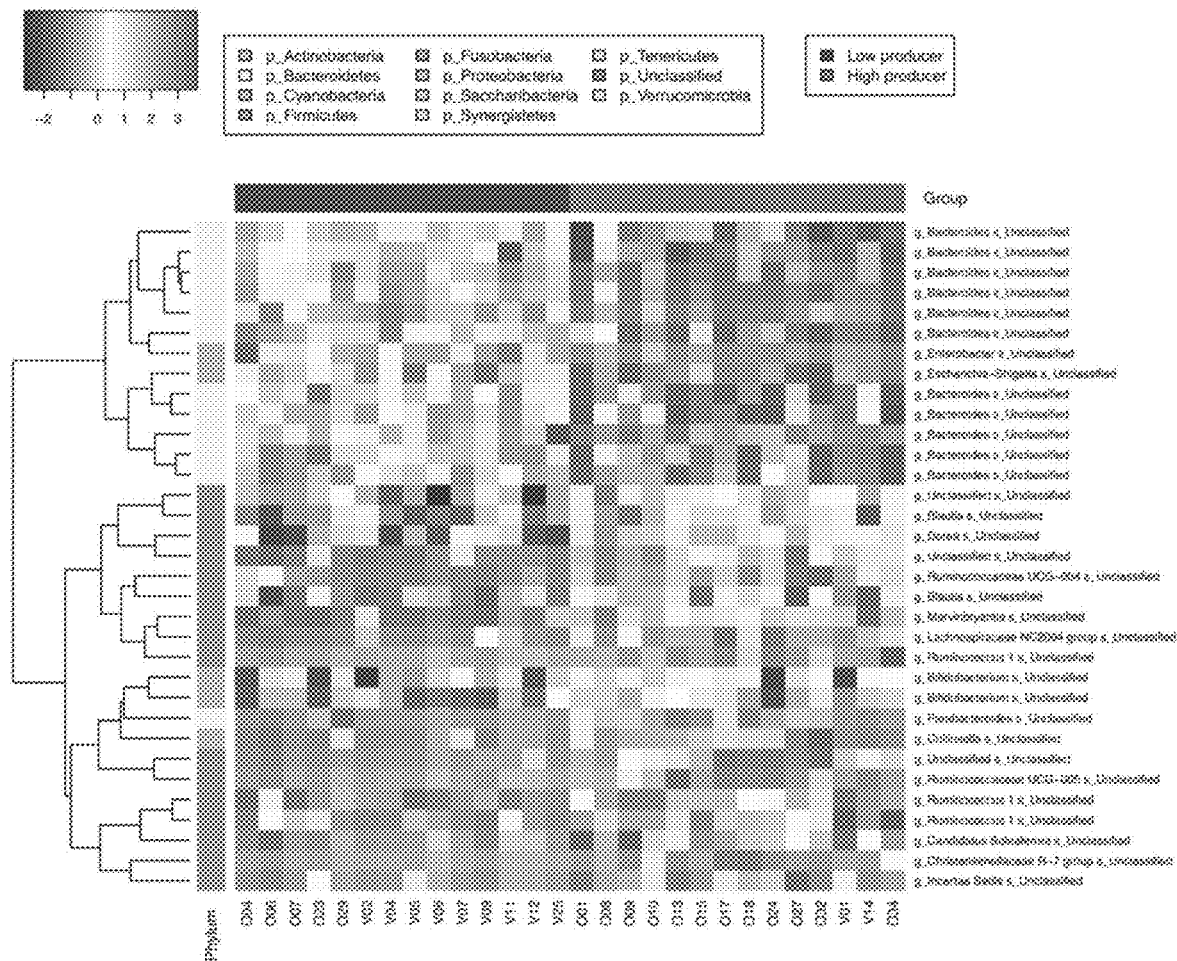
Figure 6:
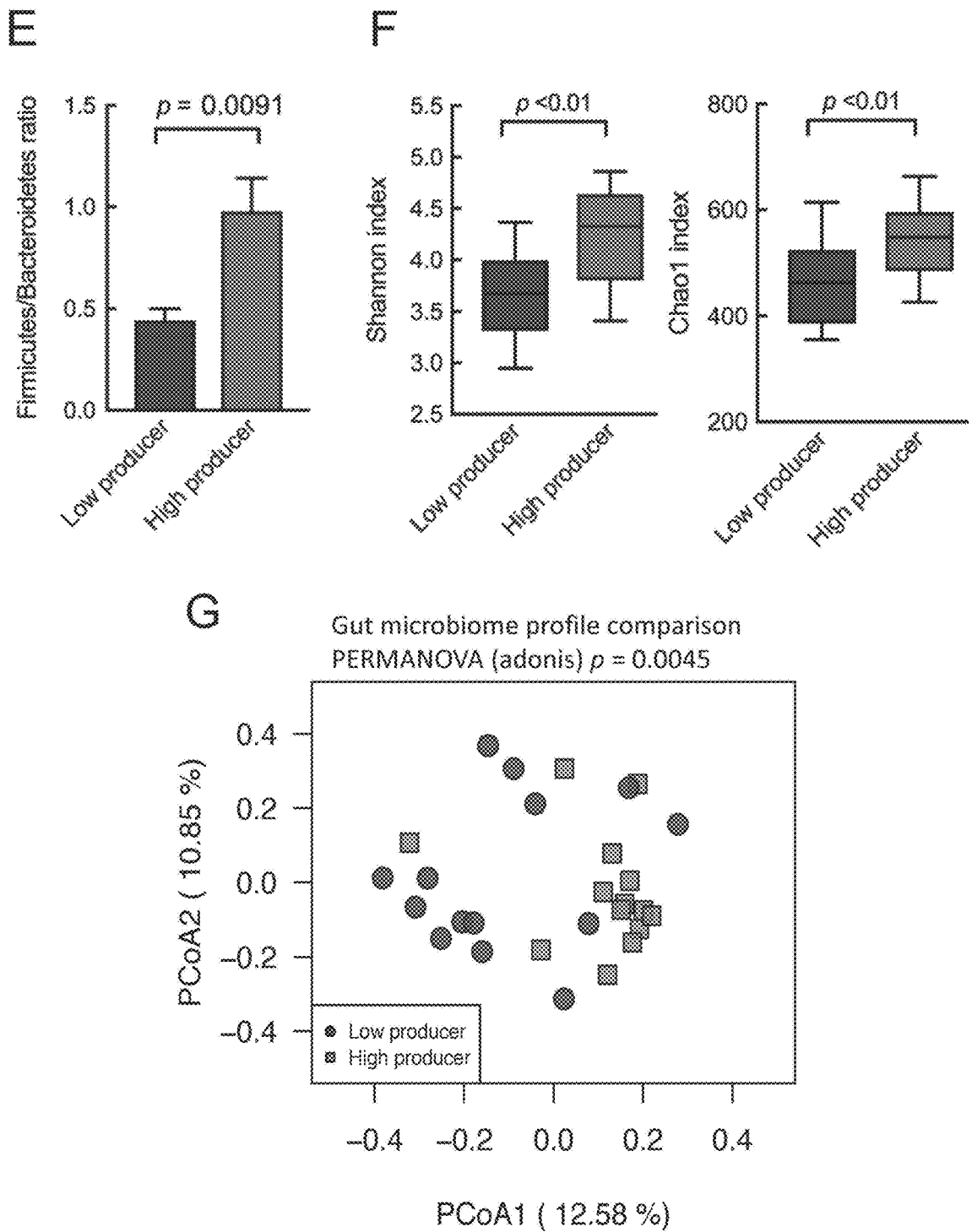
Figure 6:
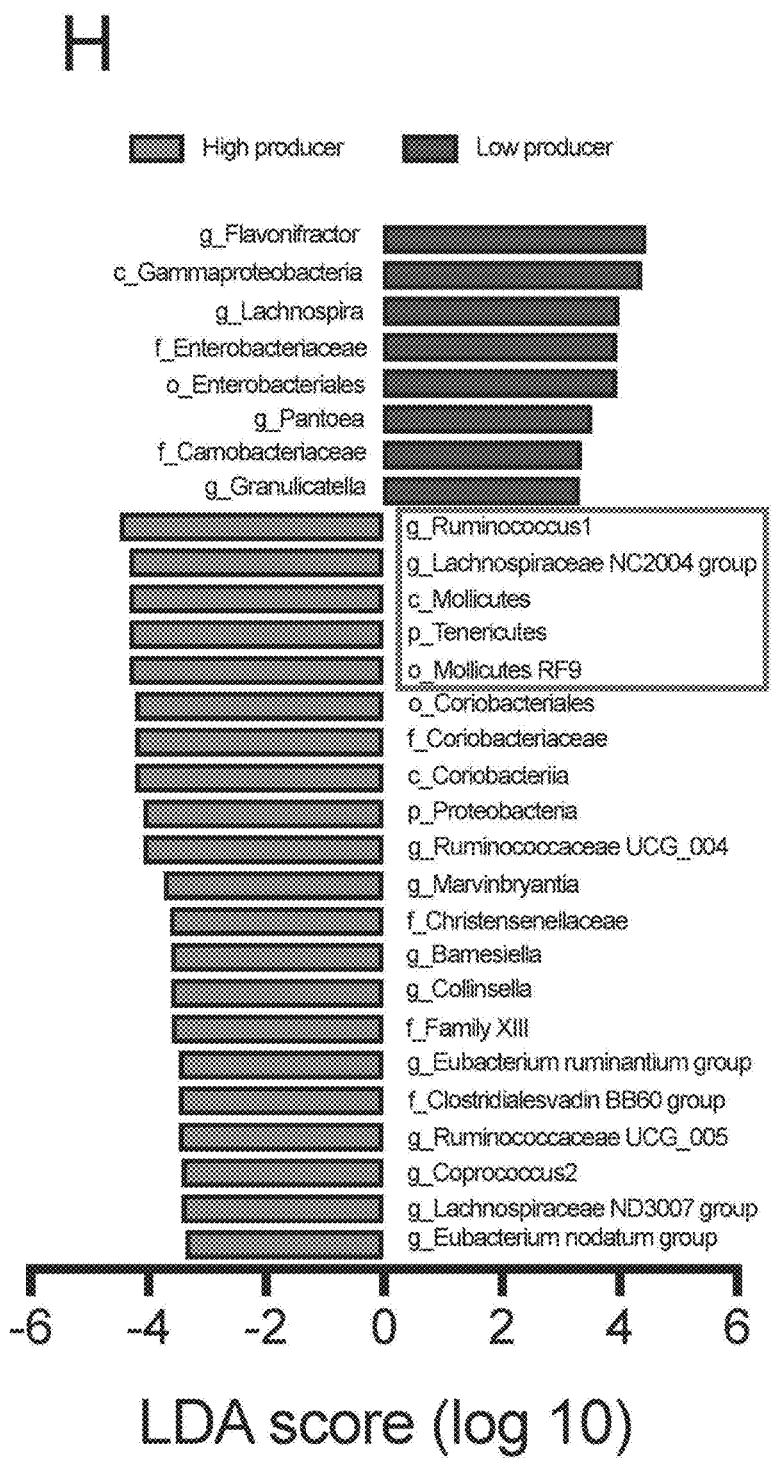
Figure 6:
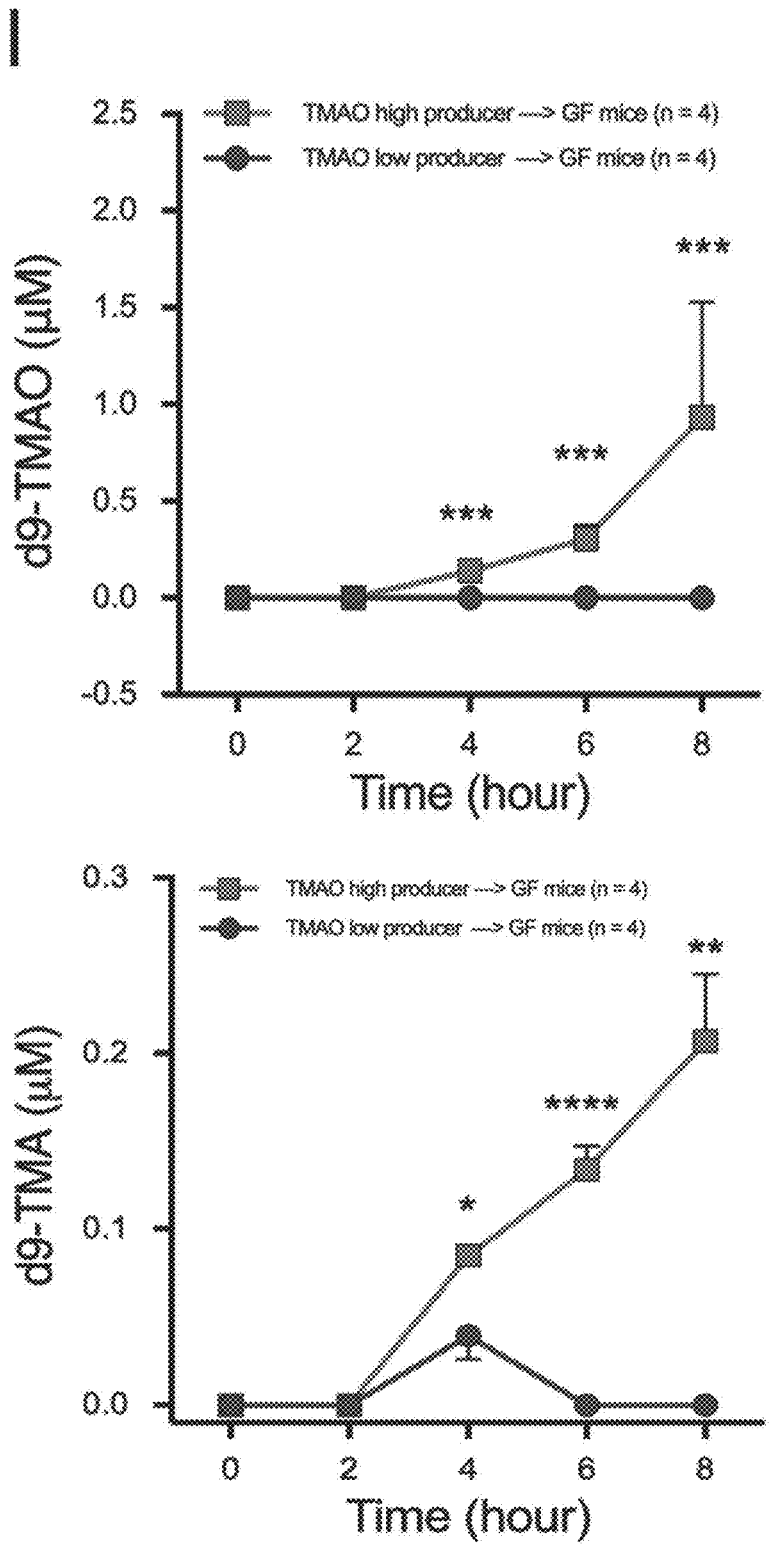

Gut microbiome profiles become distinctive after functional phenotyping of TMAO production capacity: In this example, the functional phenotypes of the high TMAO producers (n=14) and low TMAO producers (n=14) identified using the OCCT corresponded with distinctive OCCT curves and significantly different AUC and $TMAO_{max}$ values (FIG. 6A-6C). However, the difference in fasting plasma TMAO levels between the high and low TMAO producers remained moderate (FIG. 6B). This finding further suggested that a challenge test of the present invention, rather than a single blood test, should be considered in clinical assessments to determine the functional phenotype of TMAO-producing gut microbiota. In addition, the compositional patterns of gut microbiome in the high versus low TMAO producers were distinctive, as demonstrated by the heatmap and principle coordinate analysis (FIGS. 6D and 6G). Other common gut microbiome functional indicators, including F/B ratio, Shannon index and Chao1 index, also indicated significant differences between the high and low TMAO producers (FIGS. 6E and 6F). The higher alpha diversity of the high TMAO producers suggested higher compositional complexity of the gut microbiome for acquiring TMA synthesis functions. The higher F/B ratio in the high TMAO producers corresponded to the findings of high-risk patients with CVD in previous studies. Furthermore, the results of the LEfSe analysis regarding the characteristic bacterial taxa between the high and low TMAO producers were similar to the results of previous mouse experiments (FIG. 6H).

TMAO-producing phenotypes determined using the OCCT were reproduced in the humanised gnotobiotic mice model: The TMAO-producing functional phenotypes determined using the OCCT were based on complex diet-gut microbiota-host interactions. Therefore, this example used a humanised gnotobiotic mouse model to reconstruct these complex interactions in vivo. Fecal microbiota transplantation (FMT) was performed on germ-free mice by using faeces from a high TMAO producer and a low TMAO producer from our study cohort. In the animal model, diet and host factors were well controlled. Eight 9-week-old male germ-free mice were divided into two groups (n=4 in each group) and performed FMT with gastric gavage in the mice of each group using faecal samples from two human donors (a high TMAO producer and a low TMAO producer). All the mice received a carnitine-supplemented diet for 5 weeks after which they underwent d9-carnitine oral challenge tests. The results demonstrated that the transplantation of gut microbiota transmitted the human host's TMAO-producing phenotypes to the mouse hosts (FIG. 6I).

Figure 7:
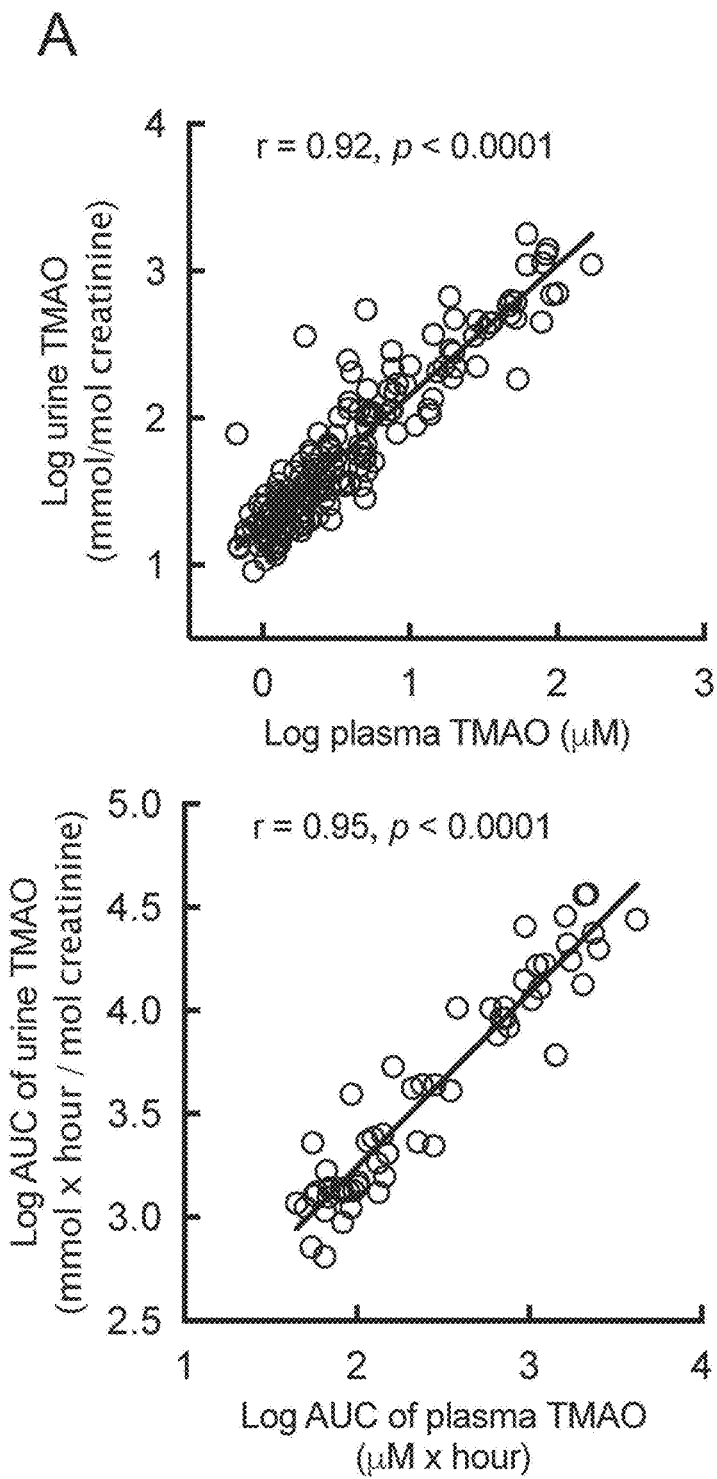
FIG. 7 shows a preferred embodiment of the present invention, which shows that urine TMAO levels exhibited strong correlation with plasma TMAO levels and may serve a substitute specimen for OCCT. The logarithmic TMAO values of 171 plasma samples strongly correlated with the corresponding TMAO values of urine samples from the same subject and sampling times. The logarithmic AUC values of plasma TMAO in 57 participants strongly correlated with the AUC values of urine TMAO in the same OCCT. Pearson's correlation was used to calculate association between two variables.

C. Result 2:

Use urine samples to perform OCCT as a method to determine TMAO production capacity in an individual: Through the aforementioned experiments, it has been proved that OCCT is the standard for measuring TMAO production capacity in individuals. However, plasma TMAO levels usually peak after 24 hours of the OCCT, and the required serial blood sampling may present challenges for clinical practice and patient compliance. Thus, the present invention further compared 171 paired blood and urine samples collected at the same times. As shown in FIG. 7, the samples exhibited a strong significant correlation of TMAO concentrations; moreover, the AUC values of 57 paired blood and urine samples from the participants who underwent the OCCT were compared and exhibited a highly significant correlation. These results suggested that urine collection may provide a substitute for blood collection in the OCCT, and this solution may increase the feasibility of the method of the present invention for clinical practice.

As above, the method for measuring TMAO production capacity in an individual using OCCT of the present invention can determine the functional status of the individual's gut microbiome with regard to the TMAO production capacity. The OCCT in the invention successfully distinguish between the omnivores and vegetarians according to their TMAO-producing ability. Using the method of the invention, the gut microbiota of high and low TMAO producers can be further characterised, and the TMAO producing phenotypes can be reproduced in germ-free mice by the faecal microbiota transplantation. In addition, the invention further provides the urine TMAO as an alternative biomarker for plasma TMAO that may facilitate the transition to clinical practice. In the era of precision medicine, the method of the invention may serve as a personalised dietary guidance for patients with CVD, an assessment tool for the therapeutic efforts of new drug development, a standard method for diet-induced thrombosis risk survey as well as a potential benchmark to investigate TMAO-relevant biomarkers in the faeces.

In the present invention, the OCCT may be used to identify individual TMAO-producing capacity from gut microbiota and thereby serve as a guidance of intervention to reduce TMAO production in the human body. For example, a low-carnitine diet may be suggested to high TMAO producers as a dietary instruction for patients with CVD. Moreover, the OCCT can simulate a postprandial TMAO and reveal pathophysiological levels of plasma TMAO in subjects. In a recent pioneer study, 18 healthy volunteers receiving continuous choline supplementation for 1 month significantly increased the fasting plasma TMAO level as well as enhanced platelet hyper-responsiveness. Therefore, the OCCT in the invention may also be used in revealing the diet-induced TMAO and assessing the correlated thrombosis potential. Finally, since the OCCT could indicate the TMAO producer phenotype, it might serve as a benchmark for further TMAO-relevant microbial biomarker investigation and validation.

As above, the method of the present invention can calculate the ability of the gut microbiome to produce TMAO in a subject by oral carnitine challenge test, i.e. by making the subject intake a specific dosage of carnitine and then detecting the TMAO level of the body fluid sample at a specific time point. In addition, it is verified by the examples that the TMAO level of blood is highly correlated with the TMAO level of urine; that is, urine samples can be used instead of blood samples for the clinical application of oral carnitine challenge test. The detection result of the oral carnitine challenge test can be used as a reference basis for the development of novel microbial markers related to TMAO production, and there is no need to use isotope-labelled carnitine. Accordingly, the method of the invention can be used as a clinically functional detection method of human gut microbiota, which can be used to identify the ability of a subject's gut microbiome to metabolize carnitine and generate trimethylamine N-oxide in the human body, and therefore to assess the risk of cardiovascular disease caused by the gut microbiome of the subject. The detection results can provide clinical applications such as dietary advice and drug treatment reference for the subjects, and can provide the research direction of biomarkers related to gut microbiota and trimethylamine N-oxide production.

The above is the detailed description of the present invention. However, the above is merely the preferred embodiment of the invention and cannot be the limitation to the implement scope of the invention, which means the variation and modification according to the invention may still fall into the scope of the invention.

What is claimed is:

1. A method for measuring the trimethylamine N-oxide (TMAO) production capacity in a subject, the method comprising the following steps:
   (a) making the subject ingest a specific dosage of carnitine; and
   (b) obtaining a body fluid sample of the subject at 24 hours and 48 hours after the subject ingests the carnitine and detecting the TMAO content in the body fluid sample,
   wherein the body fluid sample of the subject is urine.

2. The method of claim 1, wherein the specific dosage is 1000-2000 mg.

3. The method of claim 1, wherein the carnitine is L-carnitine.

4. The method of claim 3, wherein the L-carnitine is in a form of L-carnitine fumarate.

5. The method of claim 1, wherein the subject fasts for at least 8 hours before step (a), a fasting body fluid sample of the subject is obtained before step (a), and the TMAO content of the fasting body fluid sample is measured and used as a reference point of the TMAO content of the subject before measuring the TMAO production capacity.

6. The method of claim 1, wherein the subject is prohibited from eating foods rich in carnitine at a specific time point after ingesting the carnitine.

7. The method of claim 1, wherein the TMAO content is related to cardiovascular disease, therapeutic drug effect assessment, and personalized diet.

* * * * *